United States Patent [19]
Torenbeek

[11] Patent Number: 4,547,308
[45] Date of Patent: Oct. 15, 1985

[54] AQUEOUS EMULSION OF TERTIARY BUTYL HYDROPEROXIDE

[75] Inventor: Reinder Torenbeek, Le Twello, Netherlands

[73] Assignee: Akzo N.V., Arnhem, Netherlands

[21] Appl. No.: 555,809

[22] Filed: Nov. 28, 1983

[30] Foreign Application Priority Data

Dec. 3, 1982 [NL] Netherlands .......................... 8204690

[51] Int. Cl.⁴ .......................... B01F 17/22; C08F 4/34; C01B 15/00
[52] U.S. Cl. .................. 252/186.26; 252/312
[58] Field of Search ........................... 252/186.26, 312; 502/160

[56] References Cited

U.S. PATENT DOCUMENTS 3,061,554 10/1962 Vartanian et al. .................. 502/160
3,825,509 7/1974 Miller .................. 502/160
3,922,173 11/1975 Misak .................. 106/194
3,988,261 10/1976 Barter et al. .................. 502/160
4,092,470 5/1978 Oosterwijk et al. .................. 526/227

FOREIGN PATENT DOCUMENTS

WO 82/00104 1/1982 PCT Int. Appl.
50-82188 7/1975 Japan .................. 252/312

Primary Examiner—Edward A. Miller
Assistant Examiner—Virginia B. Caress
Attorney, Agent, or Firm—Parkhurst & Oliff

[57] ABSTRACT

Aqueous emulsion of tertiary butyl hydroperoxide containing a protective colloid insuring stability after a storage period of two months. The protective colloid used is hydroxyethyl cellulose having a degree of substitution of more than 2.0, particularly 2.3–3.0. The emulsion may contain 0.1–10% by weight of the colloid and, optionally, up to 5% by weight of a surfactant.

6 Claims, No Drawings

AQUEOUS EMULSION OF TERTIARY BUTYL HYDROPEROXIDE

BACKGROUND OF THE INVENTION

The present invention relates to an aqueous emulsion of a tertiary butyl hydroperoxide containing a protective colloid. An emulsion of the same kind is disclosed in U.S. Pat. No. 3,061,554. The emulsion described in Example 3 of said patent specification contains polyvinyl alcohol as protective colloid and a hydrogenated tallow amide as surface active agent. After one month this emulsion was found to phase-separate. Transporting these unstable emulsions in large quantities is not without explosion hazards. For there is the change then of local concentration of the hydroperoxide as a result of phase separation and the ensuing risk of autocatalytic decomposition.

Tertiary butyl hydroperoxide is therefore marketed as a mixture saturated with water or di-tertiary butyl peroxide. Such mixtures contain 70 to 80% by weight of tertiary butyl hydroperoxide and 20 to 30% by weight of water or di-tertiary butyl peroxide. Although these formulations are considered relatively safe, the explosion hazard during storage and transport must still be reckoned with because of the relatively high peroxide content of these mixtures. Another possibility consists in preparing aqueous solutions containing up to about 18% by weight of tertiary butyl hydroperoxide. Because of their low peroxide content, however, such solutions can hardly be considered attractive from an economical point of view, particularly in the case of transporting and storing large quantities.

There is consequently a need for stable aqueous formulations containing 20 to 70% by weight of tertiary butyl hydroperoxide. Intensively mixing the two components, optionally in the presence of one or more surface active agents, merely results in unstable formulations. For when at rest, these compositions were found to rapidly phase-separate into two layers, the upper one consisting of tertiary butyl hydroperoxide (about 70%) saturated with water and the lower one of water saturated with tertiary butyl hydroperoxide (about 20%). Also found to be unstable were formulations to which as protective colloid there had been added carboxymethyl cellulose, methyl cellulose, hydroxypropyl cellulose, polyvinyl alcohol, polyvinyl pyrrolidone, polyacrylic acid, carboxyvinyl polymer, xanthan gum, gelatin, starch or agar.

Tertiary butyl hydroperoxide is used for the preparation of numerous other peroxy compounds, such as tertiary butyl perbenzoate, tertiary butyl peroxyacetate and tertiary butyl peroxypivalate. Tertiary butyl peroxypivalate is also used as initiator in the polymerization of acrylates, in preparation of acrylonitrile butadiene-styrene terpolymers, polystyrene and copolymers of styrene and butadiene.

It should be added that U.S. Pat. No. 3,061,554 describes stable, aqueous pinane hydroperoxide emulsions. Moreover, U.S. Pat. No. 3,825,509 describes stable, aqueous hydroperoxide emulsions in which 1-5% by weight of polyvinyl alcohol and 1-6% by weight of polyoxyethylene sorbitan monolaurate are incorporated. Such a stabilizing system, however, is unsuitable for preparing stable emulsions of tertiary butyl hydroperoxide. Frozen emulsions of certain organic peroxides in concentrations of 30-70% peroxide stable to freeze—thaw cycles are described in U.S. Pat. No. 3,988,261. However, the disclosure does not relate to hydroperoxides, let alone tertiary butyl hydroperoxide.

SUMMARY OF THE INVENTION

The present invention meets the above-mentioned need and relates to an emulsion of the above-mentioned type, which is characterized in that the protective colloid is a hydroxyethyl cellulose having a degree of molar substitution (M.S.) higher than 2.0. It has been found that aqueous emulsions of 20-70% by weight of tertiary butyl hydroperoxide containing 0.1-10% by weight hydroxyethyl cellulose having a M.S. higher than 2.0 are stable and permit handling and storage without any explosion hazards whatsoever.

The term "stable emulsions" as used herein refers to emulsions which, after being allowed to stand for two months at 20° C., do not display any phase separation or formation of flock.

DETAILED DESCRIPTION OF THE PREFERRED EMBODIMENT

The present stable emulsions contain 20 to 70% by weight, preferably 30 to 50% by weight, of tertiary butyl hydroperoxide and an effectively stabilizing amount of hydroxyethyl cellulose having a degree of molar substitution higher than 2.0 as a protective colloid. Amounts of the protective colloid in the range of 0.1 to 10% by weight, and preferably 0.2 to 4% by weight, are effective.

Hydroxyethyl cellulose is prepared from cellulose by replacing the hydroxyl groups with hydroxyethyl groups by reacting the cellulose with sodium hydroxide and ethylene oxide. In this reaction, the three hydroxyl groups per anhydroglucose unit may be replaced and additional ethylene oxide may be reacted with the hydroxyl groups of already introduced hydroxyethyl groups to form side chains. The average number of moles of ethylene oxide introduced per anhydroglucose unit is referred to as degree of molar substitution (M.S.). According to the invention this degree of molar substitution should be higher than 2.0, generally not above 10 and should preferably be in the range of 2.3 to 3.0. Particularly suitable for use are hydroxyethyl celluloses having a degree of molar substitution of about 2.5. Examples of commercially available products having such degree of molar substitution include Natrosol 250 HHR ®, Natrosol 250L ®, Natrosol 250 G ®, Natrosol 250 K ®, Natrosol 250 M ®, Natrosol 250 HR ® (of Hercules Inc.), Culminal HEC 400 PR ® and Culminal HEC 5000 PR ® (of Henkel). These hydroxyethyl celluloses only differ in molecular weight, so that when used in the same amount emulsions of different viscosities are obtained.

Optionally, the present emulsions may contain one or more surface active agents. To that end use may be made of anionic, cationic or non-ionic surface active agents. Examples thereof are mentioned in U.S. Pat. No. 3,988,261, the specification of which is hereby incorporated by reference. Particularly suitable for the preparation of the present emulsions are ethoxylated sorbitan monolaurates. Generally, the composition may contain up to 5% by weight, preferably 0.2-2.0% by weight, of one or more surface active agents.

The emulsions may be prepared in the usual manner by, say, dissolving the hydroxyethyl cellulose and, optionally, the emulsifier(s) in water and adding tertiary butyl hydroperoxide, with stirring.

Generally, an emulsion of the "oil-in-water" type is obtained then; or when use is made of the appropriate surface active agent, a "water-in-oil" emulsion may be obtained.

The invention will be further described in the following examples.

EXAMPLE 1

In a beaker, 30 g of hydroxyethyl cellulose having a degree of molar substitution of 2.5 (Natrosol 250 L ®) were dissolved in 380 ml of water.

Subsequently, 590 g of tertiary butyl hydroperoxide (70%) were added dropwise with high speed stirring using a turbine agitator. A stable emulsion was formed, which did not show any separation after two months storage at 20° C.

EXAMPLE 2

In a beaker, 3 g of hydroxyethyl cellulose having a degree of molar substitution of 2.5 (Natrosol 250 HHR ®) were dissolved in 396 ml of water. As emulsifying agent, 10 g of ethoxylated sorbitan monolaurate (Tween 20 ®) were added. Subsequently, 590 g of 70% by weight tertiary butyl hydroperoxide were added dropwise with high speed stirring using a turbine mixer. During the addition, first of all the peroxide dissolved to form a clear solution in water until the saturation point was reached. Next, the mixture turned white and a homogeneous emulsion was formed. After 2 months at 20° C., this emulsion still did not show any separation and also the active oxygen content of the peroxide had remained unchanged.

To demonstrate the stability imparted to the t-butyl hydroperoxide by the invention, the limit of disk aperture in the pressure vessel was measured and was found to be less than 1.0 mm (that of 70% by weight tertiary butyl hydroperoxide and 30% by weight water is 3.0 mm). Also, the impact sensitivity (including air) was 5 kgm (for 70% by weight tertiary butyl hydroperoxide the impact sensitivity is 0.4 kgm). The limit of disk aperture of the pressure vessel and the impact sensitivity were determined by the methods as described in VSG/RID, (European Train Transport Regulations) Appendix 1, marginal numbers 1154 and 1155.

COMPARATIVE EXAMPLE 1

In a beaker 4 g of methylhydroxybutyl cellulose (Methocel HB ® of Dow Chemical Company) were dissolved in 396 ml of water. As surface active agent there was added 10 grams of ethoxylated sorbitan monolaurate (Tween 20 ® of ICI).

Subsequently, there were added dropwise with high speed stirring using a turbine mixer, 590 g of tertiary butyl hydroperoxide (70%). In the process of adding said substance a precipitate formed. After all the tertiary butyl hydroperoxide had been added, stirring was continued for 10 minutes. The resulting emulsion contained 0.4% of methylhydroxybutyl cellulose. Separation set in immediately and within one hour the emulsion had completely separated into two phases.

COMPARATIVE EXAMPLES 2-16

The procedure of Comparative Example 1 was used in trying to prepare tertiary butyl hydroperoxide emulsions using different protective colloids. The results of these experiments are given in Table 1 below.

TABLE 1

Results of Comparative Examples 2-16

| Ex. | Protective Colloid Type | Wt. % | Behavior during and/or after emulsification |
|---|---|---|---|
| 2 | hydroxypropyl cellulose M.S. = about 4 (Klucel M ® of Hercules Inc.) | 0.5 | thready precipitation immediate separation |
| 3 | hydroxypropyl cellulose M.S. = about 4 (Klucel J ® of Hercules Inc.) | 1.5 | total separation within 4 days |
| 4 | methylhydroxypropyl cellulose M.S. = 0.13-0.25 (Methocel F50 ® of Dow Chem.) | 0.8 | precipitation, immediate separation |
| 5 | methylhydroxypropyl cellulose MS = 0.15-0.40 (Methocel K100 ® of Dow Chem.) | 1.0 | separation within 1 hour |
| 6 | methyl cellulose (MC25S ® of Henkel) | 2.0 | separation within 30 min. |
| 7 | methyl cellulose (C 2006 K25 ® of Henkel) | 0.8 | immediate separation |
| 8 | polyvinyl alcohol (Mowiol 18-88 ® of Hoechst) | 0.8 | virtually total separation after 3 days |
| 9 | polyvinyl alcohol (Mowiol 18-88 ®) | 2.0 | total separation after 5 days |
| 10 | polyvinyl alcohol (Gohsenol KP-08 ®. Nippon Goshei) | 2.0 | separation within 30 min. |
| 11 | xanthan gum (Rhodopol 23 ® of Rhone Poulenc) | 0.2 | separation within 30 min. |
| 12 | carboxyvinyl polymer (Carbopol 934 ® of BF Goodrich) | 0.4 | separation within 1 hour |
| 13 | polyvinyl pyrrolidone (PVP-K90 ® of GAF) | 0.8 | skin-like precipitation during emulsification, separation within 30 min. |
| 14 | polyvinyl pyrrolidone | 3.0 | see 13 |
| 15 | polymethylvinylether/maleic anhydride (Gantrez AN 169 ® of GAF) | 0.8 | precipitation during emulsification, separation within 30 min. |
| 16 | Guar-gum | 0.85 | immediate separation |

COMPARATIVE EXAMPLES 17-20

Compositions were prepared using the same procedure as in comparative Example 1, except that the tertiary butyl hydroperoxide concentration in the formulation obtained was 40% and as protective colloid hydroxyethyl cellulose was used having a degree of molar substitution equal to or lower than 2.0. To the composition there was added 1% of ethoxylated sorbitan monolaurate (Tween 20 ®). The results are given in the following Table 2.

TABLE 2

Results of Comparative Examples 17-20

| Ex. | Hydroxyethyl cellulose M.S.* | wt. % | Behavior during and/or after emulsification |
|---|---|---|---|
| 17 | 1.5 (Natrosol 150 HHWR ®) | 0.25 | separation after 5 days |
| 18 | 1.8 (Natrosol 180 GR ®) | 1.0 | separation after 4 days |
| 19 | 1.8-2.0 (Cellosize 300 H ®) | 1.0 | separation after 1 hour |

TABLE 2-continued

Results of Comparative Examples 17-20

| Ex. | Hydroxyethyl cellulose M.S.* | wt. % | Behavior during and/or after emulsification |
|---|---|---|---|
| 20 | 1.8-2.0 (Cellosize QP-09) | 4.0 | separation after 1 hour |

*M.S. = degree of molar substitution

EXAMPLES 3-5

Emulsions according to the invention were prepared using the same procedure as given in the Comparative Examples 17-20, adding ethoxylated sorbitan monolaurate (Tween 20 ®) in amounts of 1.0, 0.8 and 1.2% by weight to Examples 3, 4 and 5, respectively. As protective colloid, however, hydroxyethyl celluloses having a degree of molar substitution of 2.5 were used in various amounts. The results are given in the following Table 3.

TABLE 3

| Ex. | % TBHP* | Hydroxyethyl cellulose Type | wt. % | Behavior during and/or after emulsification |
|---|---|---|---|---|
| 3 | 40 | Natrosol 250 M ® | 1.0 | no separation after 2 months at 20° C. |
| 4 | 50 | Natrosol 250 HHR ® | 0.2 | no separation after 2 months at 20° C. |
| 5 | 30 | Natrosol 250 HHR ® | 0.5 | no separation after 2 months at 20° C. |

*TBHP = tertiary butyl hydroperoxide

EXAMPLE 6

In a breaker 20 g of hydroxyethyl cellulose having a degree of molar substitution of 2.5 (Natrosol 250 L ®) were dissolved in 400 ml of water. Successively, 10 g of an ethoxylated linear secondary fatty alcohol (Tergitol 15S12 ®) and 570 g of tertiary butyl hydroperoxide were added with high speed stirring. A stable emulsion was obtained which did not show any separation after two months' storage at 20° C.

I claim:

1. A stable aqueous emulsion of tertiary butyl hydroperoxide comprising 20 to 70% by weight of said tertiary butyl hydroperoxide and 0.1 to 10% by weight of hydroxyethyl cellulose having a degree of molar substitution greater than 2.0.

2. The aqueous emulsion of claim 1, wherein said emulsion contains up to 5% by weight of a surface active agent.

3. A stable aqueous emulsion of tertiary butyl hydroperoxide comprising 20 to 70% by weight of said tertiary butyl hydroperoxide and 0.1 to 10% by weight of hydroxyethyl cellulose having a degree of molar substitution in the range of 2.3 to 3.0.

4. The aqueous emulsion of claim 3, wherein said emulsion contains up to 5% by weight of a surface active agent.

5. The aqueous emulsion of claim 3, wherein the hydroxyethyl cellulose has a degree of molar substitution of about 2.5.

6. The aqueous emulsion of claim 5, wherein said emulsion contains up to 5% by weight of a surface active agent.

* * * * *

UNITED STATES PATENT AND TRADEMARK OFFICE
CERTIFICATE OF CORRECTION

PATENT NO. : 4,547,308
DATED : October 15, 1985
INVENTOR(S) : Reinder TORENBEEK

It is certified that error appears in the above-identified patent and that said Letters Patent is hereby corrected as shown below:

Column 1, line 15, change "change" to --chance--.

Signed and Sealed this

Fourteenth Day of January 1986

[SEAL]

Attest:

DONALD J. QUIGG

Attesting Officer

Commissioner of Patents and Trademarks